United States Patent [19]

Mickle et al.

[11] Patent Number: 4,877,810
[45] Date of Patent: Oct. 31, 1989

[54] PROTECTION OF HEART TISSUE FROM REPERFUSION INJURY

[75] Inventors: Donald A. G. Mickle; Tai-Wing Wu, both of Toronto, Ontario, Canada

[73] Assignee: Eastman Kodak Company, Rochester, N.Y.

[21] Appl. No.: 152,501

[22] Filed: Feb. 5, 1988

[51] Int. Cl.⁴ .............................................. A61K 31/35
[52] U.S. Cl. .................................... 514/456; 514/474
[58] Field of Search ........................................ 514/456

[56] References Cited

U.S. PATENT DOCUMENTS 3,903,317  9/1975  Cort .................................... 426/545
3,986,980  10/1976  Cort .................................... 426/268

OTHER PUBLICATIONS

S. Marubayashi et al., "Role of Free Radicals in Ischemic Rat Liver Cell Injury: Prevention of Damage by α-tocopherol Administration", Surgery 99, 184–192, (1986).
R. Ferrari et al., "Role of Oxygen in Myocardial Ischemic and Reperfusion Damage Effect of alpha-tocopherol", Acta Vitaminol. Enzymol 7 Suppl., 61–70 (1985), Medline Abst. No. 87045647.
A. F. Casini et al., "Liver Gluthatione Depletion Induce by Bromobenzene, Iodobenzene, and Diethylmaleate Poisoning and Its Relation to Lipid Peroxidation and Necrosis", Am. J. Pathol. 118, 225–237, (1985).
M. Khuzhamberdiev, "Activation of Lipid Peroxidation in Chronic Ischemic Heart Disease", Bull. Exp. Biol. Med. 100, 1179–1181, (1985).
"Evidence of Myocardial Free Radical Injury During Elective Repair of Tetralogy of Fallot", Circulation, vol. 76, Supplement V, Nov. 1987, pp. v174–v179.
"Free Radicals and Myocardial Ischemia and Reperfusion Injury", J. Lab. Clin. Med., Jul., 1987, pp. 13–30.
"Oxygen Free Radicals Linked to Many Diseases", Science, Research News, 30 Jan. 1987, pp. 529–531.
"Peroxy Free Radicals, Enzymes and Radiation Damage: Sensitisation by Oxygen and Protection by Superoxide Dismutase and Antioxidants", The British Journal of Radiology, 58, pp. 251–256, Mar., 1985.
"The Protective Effect of Vitamin E on Cerebral Ischemia", Surg. Neurol, 1984; 22, pp. 449–454.
"Reduction in Experimental Infarct Size by Recombinant Human Superoxide Dismutase: Insights Into the Pathophysiology of Reperfusion Injury", Circulation 74, No. 6, pp. 1424–1433.
"Antioxidant and co-Antioxidant Activity of Vitamin C. The Effect of Vitamin C, Either Alone or in the Presence of Vitamin E or a Water-Soluble Vitamin E Analogue, Upon the Peroxidation of Aqueous Multilamellar Phospholipid Liposomes", Biochimica et Biophysica Acta 835, 1985, pp. 298–303.

Primary Examiner—Frederick E. Waddell
Attorney, Agent, or Firm—Irving Newman

[57] ABSTRACT

Administration of chroman, 6-hydroxy-2,5,7,8-tetramethyl-chroman-2-carboxylic acid, prior to or simultaneously with resuming normal blood supply to the heart following ischemia provides substantial protection from tissue damage that otherwise is observed upon reperfusion of the heart.

18 Claims, No Drawings

PROTECTION OF HEART TISSUE FROM REPERFUSION INJURY

FIELD OF THE INVENTION

This invention relates to the prevention or reduction of heart tissue damage that generally has been observed to occur upon reperfusion of the isochemic heart following myocardial infarction or cardiovascular surgery (including heart transplants).

DESCRIPTION RELATIVE TO THE PRIOR ART

A number of causes and mechanisms have been suggested for the damage that occurs to myocardial tissue after ischemia and reperfusion. While it is likely that a variety of causes and mechanisms contribute to the damage, a popular current theory that is supported by experimental evidence involves the generation of free radicals upon reperfusion. One recent publication, "Evidence of Myocardial Free Radical Injury During Elective Repair of Tetralogy of Fallot," CIRCULATION, Vol. 76 Supplement V, page v-174, November 1987, indicates that lipid peroxidation (probably caused by an oxygen mediated free radical mechanism) occurs in pediatric patients during surgery to correct Tetralogy of Fallot. The current consensus on the role of free radicals in reperfusion injury is discussed in a recent review article entitled "Free radicals and myocardial ischemia and reperfusion injury," J LAB CLIN MED, July, 1987, which lists 146 references. See also J. L. Marx, "Oxygen Free Radicals Linked to Many Diseases," SCIENCE, RESEARCH NEWS, Jan. 30, 1987, pp. 529–531.

Both Vitamin E (alpha-tocopherol), which is very lipophilic, and its somewhat more water soluble derivative, 6-hydroxy-2,5,7,8-tetramethyl-chroman-2-carboxylic acid (also known as Trolox-C, hereinafter sometimes referred to as TX-C for convenience), are known antioxidants that have been used as food additives to retard spoilage. Both are chromans; their structures are shown below.

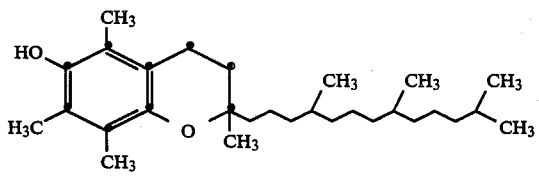

VITAMIN E

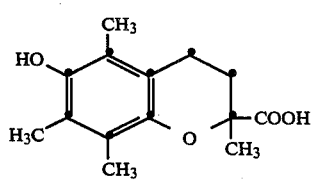

TX-C

In vitro studies showing the efficacy of Trolox C and of Vitamin C in the protection of enzymes from free radical damage caused by radiation exposure in the presence of thymine are reported in an article in THE BRITISH JOURNAL OF RADIOLOGY, 58, 251–256 (1985) entitled, "Peroxy free radicals, enzymes and radiation damage: sensitisation by oxygen and protection by superoxide dismutase and antioxidants". The data reported in FIG. 4 of that article indicate that substantially equal protection is afforded in that in vitro model by Trolox C, Vitamin C and the highest concentration used of SOD (superoxide dismutase).

While it has been reported that Vitamin E was found to be effective to some degree in vivo in providing protection to the brain from cerebral ischemia in the "canine model of the complete ischemic brain regulated with a perfusion method," (SURG NEUROL 1984; 22:449–54 "The Protective Effect of Vitamin E on Cerebral Ischemia," we are not aware of any reported in vivo experiments using Trolox C, particularly in work with the ischemic heart. Moreover, those skilled in the art know it would be impractical to attempt to employ Vitamin E infusions under the commonly encountered conditions of heart ischemia in order to provide protection from reperfusion injury, because of the insolubility of Vitamin E in water as well as the ease with which it is oxidized (with resultant loss in efficacy).

To date, the most efficacious in vivo treatment that has been reported for preventing reperfusion injury in the ischemic heart has been provided by SOD. Thus, for example, in "Reduction in experimental infarct size by recombinant human superoxide dismutase: insights into the pathophysiology of reperfusion injury," CIRCULATION 74, No. 6, 1424–1433, 1986, Ambrosio et al report that SOD perfusion (alone or together with catalase) simultaneously with reperfusion of the ischemic dog heart resulted in an infarct size of only 33.6% of the risk region as compared to 52.2% of the risk region in control dogs, a significant 36% improvement.

As reported hereinafter, we have surprisingly found that the treatment of the present invention provides even greater protection than that reported for SOD (infarct of 8.2% of the risk region vs. 27.4% for the control, an improvement of about 80%).

SUMMARY OF THE INVENTION

Thus, we have discovered that administration of Trolox C, preferably dissolved in saline, substantially concurrently with reperfusion of an ischemic heart, is a very effective way to prevent or minimize reperfusion injury.

More particularly, in accordance with the present invention there is provided a method for protecting the heart of a mammal from tissue injury that is associated with reperfusion of an ischemic heart which method comprises introducing into the blood circulation of said mammal an amount effective to inhibit reperfusion injury of the chroman compound 6-hydroxy-2,5,7,8-tetramethyl-chroman-2-carboxylic acid.

In another aspect, the present invention provides a composition for protecting the heart of a mammal from tissue injury associated with reperfusion after ischemia, said composition comprising an effective amount of 6-hydroxy-2,5,7,8-tetramethylchroman-2-carboxylic acid in a pharmaceutically acceptable vehicle.

In yet another aspect, the present invention provides a process for preparing a preferred composition for carrying out the treatment of the present invention, this process comprising:

(1) bubbling nitrogen through physiological saline solution for a period of from about 2 to about 3 hours in order to reduce the oxygen content of said solution;

(2) adding from about 25–50 mg of ethylenediaminetetraacetic acid (EDTA) per liter of the saline solution while continuing said nitrogen bubbling;

(3) adding approximately 4–6 gm of ascorbic acid per liter of the saline solution while continuing nitrogen bubbling;

(4) adding from about 3 to about 5 gm of TX-C per liter of saline while stirring and bubbling nitrogen;

(5) slowly (over a period of approximately 2 to 10 minutes) adding sodium hydroxide to adjust the pH of the resulting solution to about 12 so as to enhance the solubility of the TX-C;

(6) adding from about 2 to about 6 gm of ascorbic acid per liter of saline solution so as to achieve a pH less than or equal to a value within the range of about 6.5 to about 8.0; and (7) slowly (over a period of approximately 2 to 10 minutes) adding sodium hydroxide if and to the extent needed to adjust the pH to a value within the range of about 6.5 to about 8.0.

DETAILED DESCRIPTION OF THE INVENTION

In preferred compositions for use in the treatment of the present invention, the TX-C is provided as a liquid solution. More preferably, the solution is a physiological saline solution comprising water, sodium chloride, TX-C, ascorbic acid and ethylenediaminetetraacetic acid. Preferably, it has a pH in the range of from about 6.5 to about 8.0. More preferably, the pH is in the range of from about 7.2 to about 7.8, most preferably about 7.4. A preferred composition in accordance with the present invention comprises physiological saline solution having added thereto about 3 to 5 grams per liter of TX-C, from about 4 to about 10 grams per liter of ascorbic acid, from about 25 to about 50 mg per liter of ethylenediaminetetraacetic acid and such amount of sodium hydroxide as is needed to provide the desired pH. The presently particularly preferred composition comprises from about 3.5 to 4.5 grams, most preferably about 4 grams, per liter of TX-C, from about 5 to about 8 grams, most preferably about 6 grams, per liter of ascorbic acid and from about 30 to about 40 mg, most preferably about 36 mg, per liter of ethylenediaminetetraacetic acid.

Other pharmaceutically acceptable vehicles may be substituted for the presently preferred vehicle described above. Thus, for example, physiological saline could be replaced by from about 2 to about 5% (wt./vol.) dextrose solution, or Ringer's lactate solution, or any other commonly used intravenous solution compatible with the active ingredients. Similarly, such vehicles or acceptable variations thereof could be adapted as needed for intramuscular or intraperitoneal administration. In addition, TX-C can be administered in cardioplegic solutions, e.g. Roe's solution, for myocardial protection during cardiovascular surgery. Moreover, any pharmaceutically acceptable oral vehicle compatible with TX-C could be used for oral administration, for example, such gels or capsules as are used for oral administration of Vitamin E.

While it is preferred to use ascorbic acid as an enhancer for TX-C in the compositions of the present invention, effective amounts of other pharmaceutically acceptable materials that are compatible with, and would prevent the oxidation of, TX-C could be substituted for all or part of the ascorbic acid. These may include, for example, mercaptoethanol, dithiothreitol, glutathione, cysteine, and the like.

The presently preferred process for preparing the presently preferred composition according to the present invention comprises the steps of:

(1) bubbling nitrogen through physiological saline solution for a period of from about 2 to about 3 hours in order to reduce the oxygen content of said solution;

(2) adding about 30 to 40 mg, most preferably about 36 mg, of EDTA per liter of the saline solution while continuing nitrogen bubbling;

(3) adding approximately 4 gm of ascorbic acid per liter of the saline solution while continuing nitrogen bubbling;

(4) adding about 3.5 to about 4.5 grams, most preferably about 4 grams, of TX-C per liter of the saline solution while stirring and bubbling nitrogen;

(5) slowly adding sodium hydroxide to adjust the pH of the resulting solution to about 12 so as to enhance the solubility of the TX-C;

(6) adding from about 1 to about 4, preferably about 2 grams, of ascorbic acid per liter of the saline solution so as to achieve a pH less than or equal to about 6.5 to about 8.0, preferably about 7.2 to about 7.8, most preferably about 7.4; and (7) slowly adding sodium hydroxide if and to the extent needed to adjust the pH to about 6.5 to about 8.0, preferably about 7.2 to about 7.8, most preferably about 7.4.

In accordance with the presently preferred treatment of the invention, the ischemic heart of a mammal is protected from reperfusion injury by intravenous or intraarterially administering to the mammal, substantially concurrently with the beginning of reperfusion of a heart to which the flow of blood has been temporarily reduced, as occurs, for example, during a heart attack or coronary surgery, a preferred composition of the present invention, the contents and preparation of which have been described above. More preferably, the administration of the composition of the present invention is begun from about 0.5 to about 5 minutes before reperfusion begins, most preferably from about 0.5 to about 1 minute before reperfusion begins and is continued for from about 2 to about 5 minutes after reperfusion has been initiated, most preferably from about 3 to about 4 minutes after initiating reperfusion.

While introduction of the compositions of the present invention directly into the bloodstream is the presently preferred route of administration, the present invention also contemplates intramuscular as well as intraperitoneal administration under appropriate circumstances. Other suitable forms of administration within the scope of the present invention include oral and cardioplegic, either alone or in combination with other forms of administration, such as those described above, particularly for such conditions as scheduled surgery involving heart by-pass.

The following example is presented to illustrate the practice of the present invention.

EXAMPLE

A solution of TX-C was prepared as follows:

500 ml of physiological saline solution was treated by bubbling nitrogen ($N_2$) through it for 2–3 hrs to decrease the $O_2$ in solution. Then, while stirring and continuing to bubble $N_2$, 18 mg of EDTA (ethylenediaminetetraacetic acid) was added, followed by 2000 mg of ascorbic acid. Then 2000 mg of TX-C was added under stirring and $N_2$ bubbling, and the pH was adjusted with NaOH to about 12 to solubilize the TX-C. A spectrally clear (homogeneous) solution was obtained within five minutes. After the TX-C was dissolved, 1000 mg ascorbic acid was added, followed by sufficient NaOH to arrive at a pH of approximately 7.4.

A canine model of 2 hours of LAD (left anterior descending artery) regional ischemia followed by 4 hours of reperfusion was used. The area at risk and the area of infarction were estimated by a dual staining technique using Evan's blue and triphenyl tetrazolium HCl infused at 100mm Hg pressure (physiological coronary perfusion pressure) after cardiac excision. More particularly, in dogs weighing between about 15 and 25 kg, the LAD was occluded for 2 hours and then reperfused for 4 hours. These were the "untreated" controls. In the same model, 500 ml of saline containing 2.0g TX-C, 3.0g ascorbic acid and 18 mg EDTA (prepared as described above) were rapidly infused into the test dogs' ascending aorta beginning 30 sec before reperfusion and then for the initial 3 min of reperfusion. After 4 hours of reperfusion, the hearts were excised and Evans blue dye and tetrazolium staining were employed to identify the areas of risk and the areas infarcted.

As shown in Table 1, medical reperfusion (control) resulted in 27.4±4.8% infarction (N=7) and the Trolox-ascorbate reperfusion produced 8.2±1.6% (N=7) infarction of the area of risk. The unpaired T-test gives a value of 3.82 with 12 degrees of freedom and a P<0.001. (To our knowledge this is the most significant decrease in regional myocardial necrosis reported to date after 2 hours of ischemia by any therapeutic intervention.)

The details of the surgical and pathology techniques employed are as follows:

In each case, a mongrel dog is anaesthetized with sodium pentobarbitol (30 mg/kg IV), intubated and ventilated with a Harvard respirator. A thoracotomy is performed under sterile conditions through the fifth left intercostal space, the left lung is gently retracted and the pericardium excised. A catheter is placed in the right femoral artery for obtaining blood gas samples. A second catheter is advanced through the left femoral artery into the central aorta for monitoring blood pressure. A third catheter is placed in the femoral vein and used for intravenous injections. The LAD is isolated just distal to the first diagonal and a 3 to 5 mm segment dissected. The heart is carefully inspected and any large collateral vessels from the right or circumflex artery are ligated near the ventricular apex to provide a reproducible region of ischemia. A doppler flow probe is placed around the LAD coronary artery and used to confirm the absence of blood flow with ischemia and the restoration of blood flow with reperfusion.

The area at risk and the area of infarction are estimated by a dual staining technique using Evans Blue and triphenyl tetrazolium hydrochloride, respectively, which are infused at 100 mm Hg pressure (physiological coronary perfusion pressure) after cardiac excision. Cannulas are inserted into the proximal aorta and into the LAD at the site of occlusion. The LAD bed is perfused with 1.5% tetrazolium in a 20 mmol phosphate buffer (pH 7.4, 38° C.) and the aorta is perfused in an antegrade manner with 0.25% Evans Blue dye.

TABLE 1

| Control Animals: | | TX-C Animals: |
|---|---|---|
| 20.0 AN/AR* | | 6.8 AN/AR |
| 21.6 | | 5.6 |
| 18.5 | | 15.9 |

TABLE 1-continued

| Control Animals: | | TX-C Animals: |
|---|---|---|
| 20.8 | | 5.5 |
| 43.6 | | 8.2 |
| 19.3 | | 4.1 |
| 47.8 | | 11.4 |
| 27.4% | mean | 8.2% |
| 4.8% | 1 SEM | 1.6% |
| 7 | N | 7 |

T test = 3.82 with 12 degrees of freedom.
P < 0.001
*Area of Necrosis (infarction)/Area at risk.

The invention has been described in detail with particular reference to preferred embodiments thereof, but it will be understood that variations and modifications can be effected within the spirit and scope of the invention.

What is claimed is:

1. A method for protecting the heart of a mammal from tissue injury that is associated with reperfusion of an ischemic heart which method comprises introducing into the blood circulation of said mammal, in an amount effective to inhibit reperfusion injury, the chroman compound 6-hydroxy-2,5,7,8-tetramethyl-chroman-2-carboxylic acid.

2. The method of claim 1 wherein said chroman compound is administered in a pharmaceutically acceptable liquid medium.

3. The method of claim 2 wherein said chroman compound is administered directly into the bloodstream.

4. The method of claim 2 wherein said chroman compound is administered intramuscularly.

5. The method of claim 2 wherein said chroman compound is administered intraperitoneally.

6. The method of claim 2 wherein said chroman compound is administered orally.

7. The method of claim 2 wherein said chroman compound is administered during a period starting from about 0.5 to about 5 minutes before initiating reperfusion and ending from about 2 to about 5 minutes after initiating reperfusion.

8. The method of claim 1 which further comprises administering to said mammal an amount of ascorbic acid sufficient to enhance the injury inhibiting effect of said chroman compound.

9. A composition for protecting the heart of a mammal from tissue injury associated with reperfusion after ischemia, said composition comprising an effective amount of 6-hydroxy-2,5,7,8-tetramethylchroman-2-carboxylic acid in a pharmaceutically acceptable aqueous carrier.

10. The composition of claim 9 which further comprises ascorbic acid.

11. The composition of claim 10 which comprises a saline solution comprising water, sodium chloride, said chroman compound, ascorbic acid and ethylenediaminetetraacetic acid.

12. The composition of claim 11 which has a pH in the range of from about 6.5 to about 8.0.

13. The composition of claim 12 wherein the pH is in the range of from about 7.2 to about 7.8.

14. The composition of claim 13 wherein the pH is about 7.4.

15. The composition of claim 12 which comprises physiological saline solution having added thereto about 3 to 5 grams per liter of said chroman compound, from about 4 to about 10 grams per liter of ascorbic acid, from about 25 to about 50 mg. per liter of ethylenediaminetetraacetic acid and such amount of sodium hydroxide as is needed to provide said pH.

16. The composition of claim 15 which comprises from about 3.5 to 4.5 grams per liter of said chroman compound, from about 6 to about 8 grams per liter of said ascorbic acid and from about 30 to about 40 mg per liter of said ethylenediaminetetraacetic acid.

17. The composition of claim 16 which comprises about 4 grams per liter of said chroman compound, about 6 grams per liter of ascorbic acid and about 36 mg per liter of EDTA.

18. A process for preparing the composition of claim 16 comprising the steps of
   (1) bubbling nitrogen through physiological saline solution for a period of from about 2 to about 3 hours in order to reduce the oxygen content of said solution;
   (2) adding said ethylenediaminetetraacetic acid while continuing said nitrogen bubbling;
   (3) adding approximately 4 gm of ascorbic acid per liter of said solution while continuing said nitrogen bubbling;
   (4) adding said chroman compound while stirring and bubbling nitrogen;
   (5) slowly adding sodium hydroxide to adjust the pH of the resulting solution to about 12 so as to enhance the solubility of said chroman compound;
   (6) adding the remaining ascorbic acid so as to achieve a pH less than or equal to a value within the range of about 6.5 to about 8.0; and
   (7) slowly adding sodium hydroxide if and to the extent needed to adjust the pH to a value within said range.

* * * * *